(12) United States Patent
Draper

(10) Patent No.: US 7,161,024 B2
(45) Date of Patent: Jan. 9, 2007

(54) PROCESS FOR THE PREPARATION AND PURIFICATION OF 2-(ALKOXYALKYLIDENE)-3-KETOALKANOIC ACID ESTERS FROM 3-KETOALKANOIC ACID ESTERS

(75) Inventor: Richard W. Draper, North Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 383 days.

(21) Appl. No.: 10/886,724

(22) Filed: Jul. 8, 2004

(65) Prior Publication Data
US 2005/0027140 A1 Feb. 3, 2005

Related U.S. Application Data

(60) Provisional application No. 60/486,227, filed on Jul. 10, 2003.

(51) Int. Cl.
*C07C 69/73* (2006.01)
(52) U.S. Cl. ..................................... 560/181
(58) Field of Classification Search ............. None
See application file for complete search history.

(56) References Cited

U.S. PATENT DOCUMENTS

| 2,824,121 | A | 2/1958 | Nicholl et al. |
| 4,808,747 | A | 2/1989 | Homann |
| 4,851,566 | A | 7/1989 | Ratton |
| 6,387,930 | B1 | 5/2002 | Baroudy et al. |
| 6,391,865 | B1 | 5/2002 | Baroudy et al. |

FOREIGN PATENT DOCUMENTS

WO WO 00/66559 11/2000

OTHER PUBLICATIONS

Claisen, L., "Uber die oxymethylenderivate des acetessigäthers, des Acetylacetons und des Malonsäureäthers," *Ber.* (1893) 26(510):2729-2735.

Claisen, L., Annalen Der Chemie. (Sep. 22, 1897) 297:1-98.
DeWolfe, Robert H., Carboxylic Ortho Acid Derivatives vol. I (1970) 231.
Emelina, E.E., et al., "Synthesis of 2-(11-Alkoxyethylidene)-1,3-Dicarbonyl Compounds," *Russian Journal of General Chemistry* (1994) 64(1):123-124.
Jones, Reuben G., "Reactions of Orthoesters with Active Methylene Compounds," *J. Am. Chem. Soc.* (Oct. 5, 1952) 74:4889-4891.
Post, Howard W., et al., "The Reactions of Ortho Esters with Certain Acid Anhydrides," *J. Org. Chem.* (1937) 2:260-266.
International Search Report—4 pgs.
Database Beilstein Beilstein Institute for Organic Chemistry, Frankfurt-Mail, DE; XP002312395 Database assession No. 4087690 cited in the application abstract & E.E. Emelina et al.: "Preparationof 4-methoxy-3-methoxycarbonyl-3-methylpentan-2,4-dione" ZH.Obshch.Khim., vol. 64, No. 1, 1994, pp. 133-134.

*Primary Examiner*—Paul A. Zucker
(74) *Attorney, Agent, or Firm*—H. Eric Fischer

(57) ABSTRACT

In its several embodiments, this invention discloses a novel process to prepare the compounds of Formula 3:

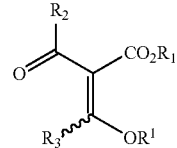

Formula 3 wherein $R^1$ is lower alkyl, and $R^2$ and $R^3$ can be the same or different, each being independently selected from the group consisting of alkyl, aryl and aralkyl; said process being carried out in a suitable solvent with at least one tert-amine carboxylate salt catalyst. The compounds of formula 3 are chemical intermediates useful for the synthesis of various heterocyclic compounds. These heterocyclic compounds are in turn useful precursors for diverse pharmaceutical, herbicidal and insecticidal agents. In particular, these intermediates are useful precursors to a variety of CCR5 inhibitors.

35 Claims, No Drawings

PROCESS FOR THE PREPARATION AND PURIFICATION OF 2-(ALKOXYALKYLIDENE)-3-KETOALKANOIC ACID ESTERS FROM 3-KETOALKANOIC ACID ESTERS

PRIORITY APPLICATION

This patent application claims the benefit of priority from U.S. provisional application, Ser. No. 60/486,227 filed Jul. 10, 2003.

FIELD OF THE INVENTION

This invention discloses a novel process to synthesize and purify 2-(alkoxyalkylidene)-3-ketoalkanoic acid esters from 3-ketoalkanoic acid esters. These products are chemical intermediates useful for the synthesis of various substituted heterocyclic compounds. These heterocyclic compounds are in turn useful precursors for diverse pharmaceutical, herbicidal and insecticidal agents. In particular, these intermediates are useful precursors to a variety of CCR5 receptor antagonists.

BACKGROUND OF THE INVENTION

The present invention is concerned with a novel process for the preparation of 2-(alkoxyalkylidene)-3-ketoalkanoic acid esters, from 3-ketoalkanoic acid esters. The process is characterized by the condensation of 3-ketoalkanoic acid esters with trialkyl orthoesters catalyzed by a tertiary amine carboxylate salt.

The reaction of orthoesters with active methylene compounds, such as 1,3-diketones, acylacetic esters, malonic esters, malononitriles and nitriloacetic esters in the presence of a catalyst, is a general reaction well known in the art for preparing 2-(alkoxyalkylidene) compounds. See Robert H. DeWolfe, *Carboxylic Ortho Acid Derivatives*, pp 231–235, Academic Press, New York, 1970. The reaction of triethyl orthoformate with various active methylene compounds in the presence of acetic anhydride has been described. See Claisen, Ber. 26, 2729, (1893), Ann 279, 16, (1897). In the case of diethyl malonate, zinc chloride was also found necessary to catalyze the reaction. Claisen also found that the substitution of acetic acid for acetic anhydride did not prove satisfactory. Other investigators have shown that acetic anhydride reacts first with the orthoester to form a diacetoxyalkoxy compound, which subsequently reacts with the active methylene compound to give the alkoxyalkylidene product. See Post et al, *J. Org. Chem.* 2, 260 (1937). Further, reactions between orthoesters and active methylene compounds proceed without acetic anhydride. See Jones, *J. Am. Chem. Soc.*, 74, 4889–4891 (1952). U.S. Pat. No. 2,824,121 discloses and claims a process for the reaction of orthoesters with various active methylene compounds catalyzed by acetic acid alone. Also, the reaction of methyl acetoacetate with trimethyl orthoacetate and ethyl acetoacetate with triethyl orthoacetate catalyzed by boron trifluoride etherate has been described. See Emeline et al, *Zh. Obshsch. Khim.*, 133–134, 64 (1994). And, U.S. Pat. No. 4,808,747 discloses the reaction of certain active methylene compounds with aldehydes and ketones, catalyzed by various metal carboxylates.

As compared with the processes known in the art, the process of the present invention produces an isolated product at a higher yield as well as a superior method of purification.

The products of the present invention, 2-(alkoxyalkylidene)-3-ketoalkanoic acid esters such as, for example, those represented by structural Formula 3, are chemical intermediates, useful for the synthesis of various substituted heterocyclic compounds.

Formula 3

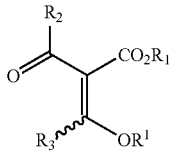

Such heterocyclic compounds include, but are not limited to, substituted pyrimidine 5-carboxylic acid esters, substituted pyrimidone carboxylic acid esters, substituted pyrazole carboxylic acid esters, substituted oxazole carboxylic acid esters and substituted 1H-pyrazolo[3,4-b]pyrid-5-ones. These substituted heterocyclic compounds are in turn useful precursors for diverse pharmaceutical, herbicidal and insecticidal agents. In particular, the substituted pyrimidine 5-carboxylic acid esters intermediates are useful precursors to a variety of CCR5 inhibitors such as, for example, those compounds discussed hereafter.

Antagonists of the CCR5 receptor are useful for the treatment of AIDS and related HIV infections. CCR5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

WO 00/66559, published Nov. 9, 2000, and U.S. Pat. No. 6,387,930, incorporated herein by reference, disclose the piperidine compound of Formula A, 4-[(Z)-(4-bromophenyl)(ethoxyimino)methyl]-1'-[(2,4-dimethyl-1-oxido-3-pyridinyl)carbonyl]-4'-methyl-1,4'-bipiperidine, its acid salt (the compound of Formula B) and pharmaceutical compositions comprising formulas A and B:

Formula A

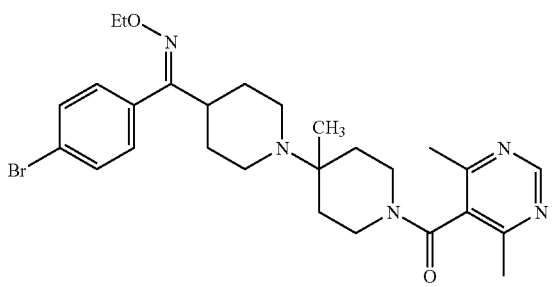

Formula B

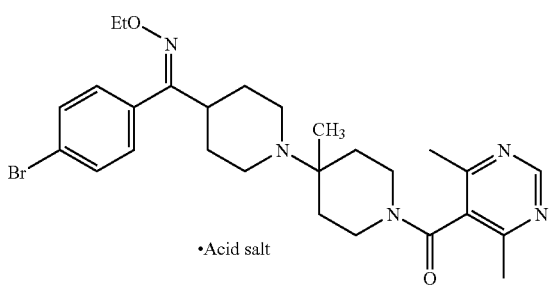

The compounds of Formulas A and B are antagonists of the CCR5 receptor and are useful for the treatment of AIDS and related HIV infections.

The piperazine compound of Formula C, piperidine, 4-[4-[(1R)-[4-(trifluoromethyl)phenyl]-2-methoxyethyl]-(3S)-methyl-1-piperazinyl]-4-methyl-1-[(4,6-dimethyl-5-pyrimidinyl)carbonyl, its acid salt (Formula D), and pharmaceutical compositions comprising the compounds of formulas C and D are disclosed in U.S. Pat. No. 6,391,865. The piperazine compound of Formula C (a free base) and its acid salt shown in Formula D, are disclosed therein as being useful as antagonists of CCR5 receptor.

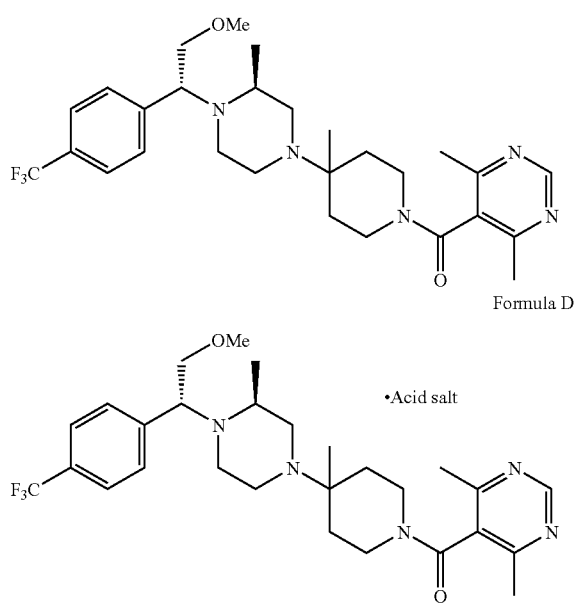

Formula C

Formula D

The inventive process described herein can be used to make 2-(alkoxyalkylidene)-3-ketoalkanoic acid esters, the compounds of Formula 3, which in general can then be used to make substituted pyrimidine 5-carboxylic acid ester intermediates. The substituted pyrimidine 5-carboxylic acid esters can then be converted to the compounds of Formulas A, B, C and D.

In view of the importance of the antagonists of the CCR5 receptor, new methods of making such antagonists including new more efficient and less expensive ways of making precursors and intermediates for the same are always of interest.

SUMMARY OF THE INVENTION

The present invention discloses a novel and easy-to-use process for preparing 2-(alkoxyalkylidene)-3-ketoalkanoic acid ester compounds of Formula 3:

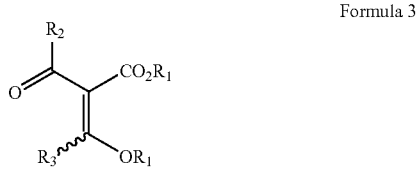

Formula 3 wherein $R^1$ is lower alkyl; and $R^2$ and $R^3$ can be the same or different, each being independently selected from the group consisting of alkyl, aryl and aralkyl; said process comprising:

reacting a 3-keto ester compound of Formula 1:

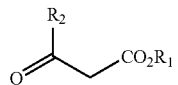

Formula 1 with an ortho ester compound of Formula 2:

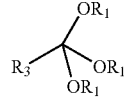

Formula 2 in the presence of at least one catalyst and at least one solvent to yield said compounds of Formula 3. The inventor found that the use of at least one tertiary amine ("tert-amine") carboxylate salt as catalyst(s) surprisingly made this process a highly efficient and economical method for producing compounds of Formula 3.

As compared to processes known in the art, the present process employing the novel catalyst(s) of the invention provides efficiency as well as a superior method for the isolation and purification of the compounds of Formula 3.

DETAILED DESCRIPTION OF THE INVENTION

As used herein the following terms have the following meanings unless otherwise defined:

Alkyl—represents straight and branched carbon chains and contains from one to twenty carbon atoms, preferably one to six carbon atoms. "Lower alkyl" means a group having about 1 to about 4 carbon atoms in the chain which may be straight or branched. The alkyl group may be substituted by one or more substituents which may be the same or different, each substituent being independently selected from the group consisting of halo, alkyl, aryl, -cycloalkyl, alkoxy and alkylthio. Non-limiting examples of suitable alkyl groups include methyl, ethyl, n-propyl, isopropyl, n-butyl, and t-butyl;

Aryl(including the aryl portion of aralkyl)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (typically to 3) with one or more of halo, alkyl, alkoxy, phenoxy and $CF_3$;

Aralkyl—represents an alkyl group, as defined above, substituted with an aryl group, as defined above, wherein the substituent (aryl group) is attached to the parent molecule through the alkyl moiety.

Unless stated otherwise alkyl, aryl and aralkyl groups can be unsubstituted or optionally substituted with one or more substituents as described herein.

The wavy line ⁓⁓⁓ as a bond generally indicates E and Z geometrical isomers.

In one embodiment, the present invention discloses a novel, easy-to-use process for preparing 2-(alkoxyalkylidene)-3-ketoalkanoic acid esters compounds of Formula 3, which can be used to prepare various pyrimidine carboxylic acids. The inventive process is schematically described in Scheme 1:

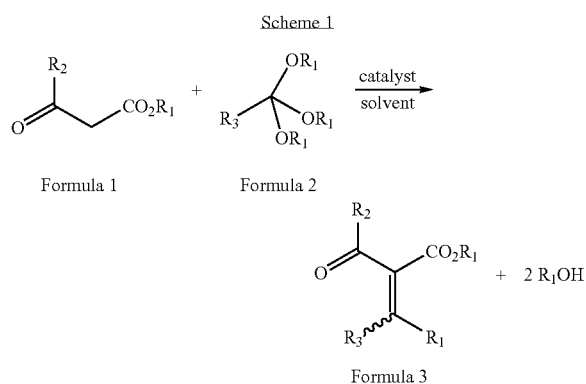

Formula 1        Formula 2

Formula 3 wherein $R_1$, $R_2$ and $R_3$ are alkyl, as defined above; preferably wherein $R_1$ is $CH_3$, and more preferably wherein $R_1$, $R_2$ and $R_3$ are all $CH_3$.

The various reaction steps outlined in the inventive process of this application contain one or more suitable solvent(s) and at least one catalyst as described below to facilitate the reaction. On completion of the reaction, the reaction may be worked up by processes known to those skilled in the art. The tert-amine carboxylate catalyst, after use in the reaction, need not be removed, which is an added advantage.

The process in Scheme 1 is preferably carried out in an organic solvent under reflux with continuous distillation of the solvent such as, for example, through a fractionating column. The alcohol by-product of the reaction co-distils with the solvent. The process is an equilibrium reaction, which is driven forward by removal of the alcohol. The latter may also be removed by absorption on molecular sieves. The solvent is selected so that not only is a suitable azeotrope formed between the alcohol and the solvent but which also has a suitable boiling point so that the starting materials mostly do not co-distil. A preferred solvent is a hydrocarbon. Non-limiting examples include toluene, benzene, heptane, cyclohexane, methyl cyclohexane and the like, or mixtures thereof. Preferred solvent is toluene (b. pt. about 111° C.), especially when $R_1$ is methyl, since toluene forms an azeotrope with methanol, distilling at about 64° C., containing about 69% by weight of methanol. The solvent n-heptane (b. pt. about 98° C.)-methanol azeotrope distils at about 59° C., containing 51% by weight of methanol; the methylcyclohexane (b. pt. about 101° C.)-methanol azeotrope distils at about 57° C., containing about 45 vol % of methanol; and the cyclohexane (b. pt. about 80° C.)-methanol azeotrope distils at about 54° C., containing about 38 vol % of methanol. Furthermore use of solvents with too high boiling points, such as m-xylene (b. pt. 139° C.) may cause considerable product decomposition and lower yields. To some extent, the choice of solvent will be dictated by the starting materials. For example, if triethyl orthoacetate (b. pt. about 142° C.) is used instead of trimethyl orthoacetate as a starting material, an azeotrope of ethanol will be distilled off. The ethanol azeotrope with toluene boils at about 77° C. containing about 68% ethanol by weight.

The reaction is preferably carried out in a vessel fitted with a jacketed Vigreux column at a temperature which causes the alcohol/solvent azeotrope to distill at the appropriate temperature (e.g. 64° C. for the methanol/toluene azeotrope). If the rate of heating is too high, the solvent will distil out too rapidly compared to the rate of alcohol formation and the temperature at the still head will increase beyond the 5 true azeotropic distilling temperature. Heating is continued and the progress of the reaction can be monitored by a suitable process such as, for example, HPLC (*see conditions below) until the formation of the product no longer increases (generally about 12–48 hours).

*Illustrative HPLC conditions for monitoring progress of the reactions:
Sample preparation: 2 drops of well agitating reaction mixture into 3 ml acetonitrile, filter
Column: YMC Pack Pro $C_{18}$ (250 mm×4.6 mm)
Column temperature: 22° C.
Eluent: Acetonitrile/water 1:1 with 0.01% TFA (0.1 ml TFA per 1000 ml mobile phase)
Gradient: isocratic
Detection wavelength: 215 nm
Injection: 10 μl
Flow rate: 1.2 ml/min
Example of Retention times:
  Methyl acetoacetate: 3.2 to 3.3 mins
  Trimethyl orthoacetate: 3.4 to 3.5 mins
  Methyl 2-acetyl-3-methoxy-2-butenoate: 3.6 to 3.7 mins The molar ratio of trialkylorthoester to 3-keto-alkanoic acid ester can be from 1:1 to 10:1, preferably from 1:1 to 2:1, most preferably from 1.2:1 to 1.5:1. The volume ratio of solvent to 3-ketoacetoalkanoic acid ester is from 10:1 to 1:1, more preferably 5:1 to 1:1, most preferably from 1.5:1 to 3.5:1.

The reaction is preferably carried out using starting materials having the same ester groups since ester interchange can occur during the reaction, giving mixtures of products. For example, methyl acetoacetate is reacted with trimethylorthoacetate or trimethylorthopropionate etc. and ethyl acetoacetate is reacted with triethylorthoacetate or triethylorthopropionate, and the like. The preferred esters groups are derived from lower alkanols, especially methyl esters and ethyl esters, as these produce a lower alcohol (methanol or ethanol respectively) during the reaction which advantageously has lower boiling points compared to the boiling points of the product and starting materials, and are more readily azeotropically distilled without distilling the product and starting materials.

The product of the reaction is conveniently isolated by, for example, distilling off the solvent and any unreacted starting materials. The residual crude product can then be purified by methods well known to those skilled in the art such as, for example, crystallization, vacuum distillation, chromatography and the like. For example, in an illustrative reaction, a purified crystalline form (m.p. 53–54° C.) of the compound represented by Formula 6 was isolated with good recoveries by crystallization from methyl t-butylether or methyl t-butylether in combination with a non-polar anti-solvent such as hexane, heptane and the like. The compound represented by Formula 6, in the crystalline form, exists as a mixture of the two geometrical isomers, the E- and Z-forms as shown by NMR spectroscopy.

The preferred catalysts in the inventive process are carboxylic acid salts of tertiary amine bases. Suitable tertiary amine carboxylic acids salts include, but are not limited to, the acetate, propionate, stearate and benzoate salts of aromatic amines such as pyridine, lutidine, quinoline, of trialkyl amines such as triethylamine, diethylisopropylamine and tributylamine, of cyclic amines such as N-methylmorpholine and N-methylpiperidine, and the like. More preferably, the catalysts include pyridinium acetate, triethylamine acetate, lutidine acetate, pyridinium propionate, triethylamine propionate, lutidine propionate and the like. The catalyst(s) is used preferably in the ratio of 1 to 100 mole % relative to the 3-ketoalkanoic acid ester. More preferred ratio is 5 to 50 mole %, and most preferred is 5 to 10 mole %.

The carboxylic acid salts of tertiary amine bases may be generated in situ by adding equimolar amounts of organic acid and organic tertiary amine base to the reaction mixture or by adding the preformed salt. In general, these carboxylic acid salts can be prepared from organic bases such as trialkylamines, triaryl-alkylamines, triarylamines, tertiary heterocyclic aromatic amines such as pyridine, lutidines, quinolines and the like, and a carboxylic acid such as alkylcarboxylic acids (e.g. acetic acid, propionic acid and butyric acid), arylcarboxylic acids (e.g. (benzoic acid and toluic acids) or aralkyl carboxylic acids such as phenylacetic acid and the like. Preferred catalysts are pyridinium acetate or pyridinium propionate.

A major advantage of using the carboxylic acid salts of tertiary amine bases is that a separate step is not required to remove them from the reaction mixture since the catalyst is soluble in the solvent system from which the product (for example the compound of Formula 6) is crystallized. Alternatively, the tertiary amine carboxylate salts remain in the residue if the product is isolated and purified by distillation.

One disadvantage of using metal acetate salts as in the traditional reactions known in the art is that additional steps are required to remove them from the reaction mixture such as by washing the reaction mixture containing compound of formula 3 with aqueous sodium citrate solution or complexation with ethylenediamine tetraacetic acid. The metal salts are not completely removed by filtration as they have some solubility in the reaction solvent and consequently could crystallize out during concentration.

The use of carboxylic acids alone, similar to that in the art, such as acetic acid and propionic acid as catalysts, in 5–10 mole % for the condensation of orthesters with acetoacetic esters was investigated for comparison purposes. In general, the reaction stopped after a few hours and additional carboxylic acid was required to restart the process. Further studies in which the carboxylic acid was refluxed in the solvent with an orthoester alone revealed that the former reacted with the latter to generate an ester of the carboxylic acid. This competitive reaction therefore consumes and is a waste of starting material. This indicated that carboxylic acid catalysts alone are not particularly useful.

While the preferred reagents and reaction conditions for the various steps are more particularly described in the Examples section, the following summarizes the details.

In still another embodiment, one or more solvents are utilized and such solvents are independently selected from the group consisting of: aliphatic hydrocarbons, alicyclic hydrocarbons, aromatic hydrocarbons, ethers, chlorinated hydrocarbons and mixtures thereof. Preferred are aliphatic hydrocarbons, alicyclic hydrocarbons and aromatic hydrocarbons. Most preferably the solvent is toluene or heptane.

In still yet another embodiment, the reaction is performed at about the reflux temperature of said solvent.

Preferably, the process utilizes the catalyst pyridinium acetate, preferably in the amount of from about 1 mole % to about 100 mole %, more preferably from about 5 mole % to about 50 mole %, or most preferably from about 5 mole % to about 10 mole %, and the reaction is carried out under reflux in a hydrocarbon solvent such as, for example, heptane or toluene, with slow distillation of the alcohol azeotrope, as described earlier.

In a preferred embodiment, the catalyst is soluble in the solvent system.

In another preferred embodiment, the products of the reactions are isolated substantially pure by techniques such as, for example, crystallization or by vacuum distillation. More preferably, the crystallization is from methyl t-butylether or methyl t-butylether in combination with a non-polar anti-solvent such as heptane and the like.

In another aspect, the present invention relates to a process comprising reacting a compound of Formula 4:

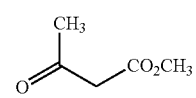

Formula 4 with a compound of Formula 5:

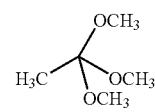

Formula 5 in the presence of at least one catalyst and at least one solvent to form the compound of Formula 6:

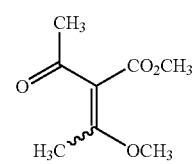

Formula 6

The various reaction steps outlined in this aspect of the inventive process of this application also contain one or more suitable solvent(s) and at least one catalyst to facilitate the reaction.

The following embodiments summarize the details of the invention as they relate to the production of the compound represented by Formula 6.

In an aspect of the present invention relative to the production of the compound represented by Formula 6, a catalyst is selected from the carboxylate salts of tert-amines. In still yet another preferred embodiment of the present invention, the catalysts is pyridinium acetate; the solvent is heptane or toluene; the reaction is performed at about the reflux temperature of the solvent system; and the compound of Formula 6 is isolated as a substantially pure crystalline material.

In still another preferred embodiment, the product of the reaction, the compound of Formula 6, is isolated substantially pure by crystallization. More preferably, the crystallization is from methyl t-butylether or methyl t-butylether, alone or in combination with a non-polar anti-solvent such as heptane and the like.

The 2-(alkoxyalkylidene)-3-ketoalkanoic acid esters of formula 3 are useful intermediates for the preparation of a variety of heterocyclic compounds. In particular, the 2-(alkoxyalkylidene)-3-ketoalkanoic acid esters can be reacted with an amidine or amidine salt and be converted in high yield to the corresponding 4,6-disubstituted pyrimidine 5-carboxylic acid esters, which without isolation can be hydrolyzed directly to the corresponding 4,6-disubtituted pyrimidine 5-carboxylic acids. A typical example is the condensation of methyl acetoacetate (Formula 4) with trimethyl orthoacetate (Formula 5) in toluene catalyzed by pyridinium acetate. The product, methyl 2-acetyl-3-methoxycrotonate (Formula 6), on reaction with amidines affords methyl 4,6-dimethylpyrimidine-5-carboxylates which can then easily be converted to their corresponding acids (Formula 7) and ultimately be used as precursors to a variety of CCR5 inhibitors. A general scheme is presented below as Scheme 3 wherein $R^5$ is H, aryl or alkyl:

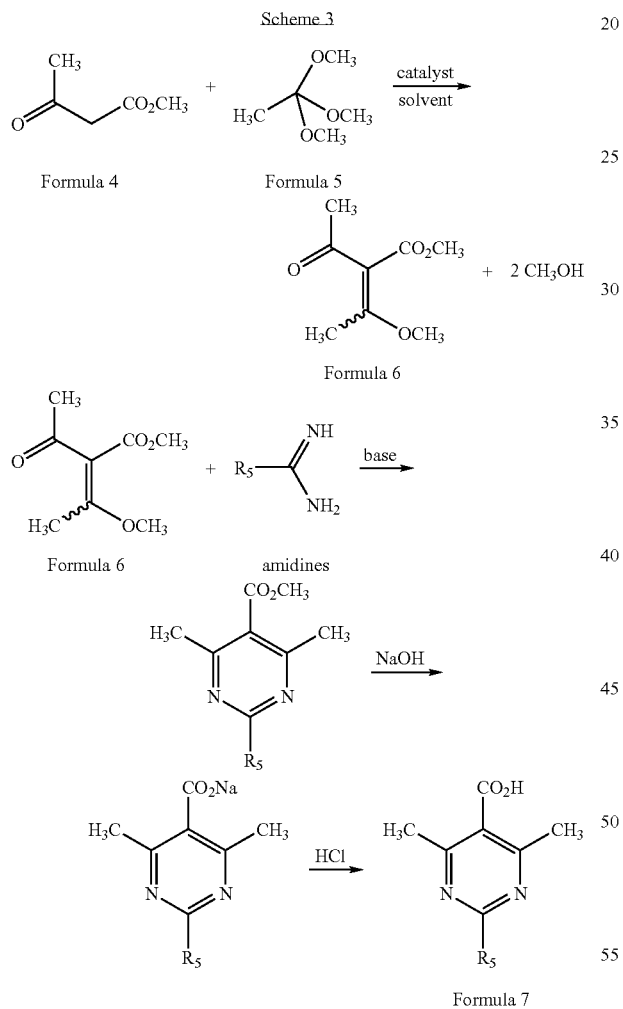

In still another particularly preferred embodiment, the present invention discloses an improved process for the preparation of 2-(alkoxyalkylidene)-3-ketoalkanoic acid esters, which does not require the separate step of removing the catalyst from the reaction medium.

In still yet another particularly preferred embodiment, the present invention discloses a process that results in products of improved purity.

The following non-limiting Examples illustrate the present invention in more details and are for illustrative purposes only. It will be apparent to those skilled in the art that many modifications, variations and alterations to the present disclosure, both to materials, methods and reaction conditions, may be practiced. All such modifications, variations and alterations are intended to be within the spirit and scope of the present invention.

Unless otherwise stated, the following abbreviations have the stated meanings below:
  b. pt.=boiling point
  $CDCl_3$=deuterochloroform
  $Cu(OAc)_2$=copper acetate
  $D_2O$=deuterium oxide
  EtOAc=ethyl acetate
  HCl=hydrochloric acid
  HOAc=acetic acid
  HPLC=high performance liquid chromatography
  KOt-Bu=potassium t-butoxide
  m.p=melting point
  NaOH=sodium hydroxide
  THF=tetrahydrofuran
  $Zn(OAc)_2$=zinc acetate
  HR-MS=High Resolution Mass Spectrometry
  NMR=nuclear magnetic resonance spectroscopy

EXAMPLES

Example 1

Preparation of E- and Z-methyl 2-acetyl-3-methoxy-2-butenoate Mixture Using Pyridine and Acetic Acid Catalyst

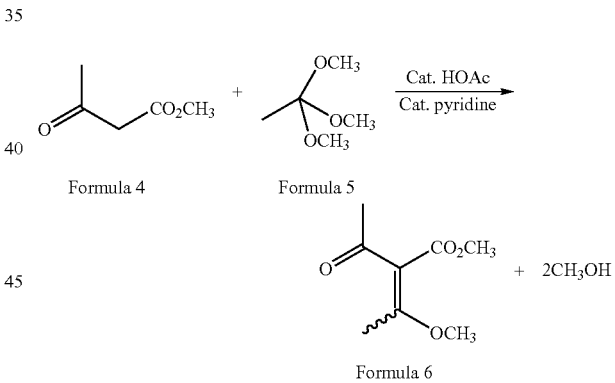

Methyl acetoacetate (108 ml, 1 mole), trimethyl orthoacetate (152 ml, 1.2 mole), toluene (270 ml), pyridine (4.04 ml, 5 mole %) and acetic acid (2.86 ml, 5 mole %) were charged into a 1 L 3-necked, flask (fitted with a 30 cm vacuum jacketed Vigreux fractionating column with stillhead and condenser, agitator, thermocouple and nitrogen inlet). The reaction was blanketed with nitrogen. The agitator was started and the flask heated to produce a very slow distillation of solvent. The heating was adjusted so that the solvent distilled at about the boiling point of the methanol/toluene azeotrope (62° C.). The distillation process was continued for about 12 hours. To the batch was charged additional pyridine (4.04 ml) and acetic acid (2.86 ml), and the slow distillation was continued for a further 12 hours. The batch was concentrated under vacuum until no more volatiles were collected at 90° C. The batch was cooled to 25–30° C. and then methyl t-butylether (324 ml), Supercel (5.0 g) and Darco (5 g) were charged to the residue. The batch was heated to reflux for 15 minutes. The batch was filtered and the Darco/Supercel cake was washed with methyl t-butylether (108 ml). The filtrate and washings were combined, then concentrated at atmospheric pressure to about 300 ml. The batch was cooled to about 25–30° C. and seeded with crystals of methyl 2-acetyl-3-methoxy-2-butenoate. Cooling the batch was continued and after crystallization commenced, began charging of heptane (216 ml) was slowly done over 40 minutes while continuing to cool the batch to −5° C. It was agitated at this temp for 2 hours. The batch was filtered and washed with cold 1:1 heptane/methyl t-butylether (216 ml) until the washings were colorless. The batch was dried for 6 hours under vacuum at 30° C. Yield of methyl 2-acetyl-3-methoxy-2-butenoate about 103 g. m.p 53–54° C. $^1$H NMR (CDCl$_3$): δ3.81 (s, OCH$_3$), δ3.79 (s, OCH$_3$), δ3.78 (s, OCH$_3$), δ3.71 (s, OCH$_3$), δ2.43 (s, CH$_3$), δ2.38 (s, CH$_3$), δ2.33 (s, CH$_3$), δ2.17 (s, CH$_3$). $^{13}$H CMR (CDCl$_3$): δ200.70, δ194.78, δ171.91, δ169.35, δ169.17, δ166.81, δ115.90, δ115.70, δ55.78, δ55.74, δ52.60, δ51.98, δ32.02, δ30.25, δ26.40, δ14.88, δ14.84. HR-MS; Calculated for C$_8$H$_{13}$O$_4$, m/z=1173.0814. Found 1173.0812.

Example 2

Preparation of methyl 2-acetyl-3-methoxy-2-butenoate Using Zinc Acetate Catalyst (a Comparison)

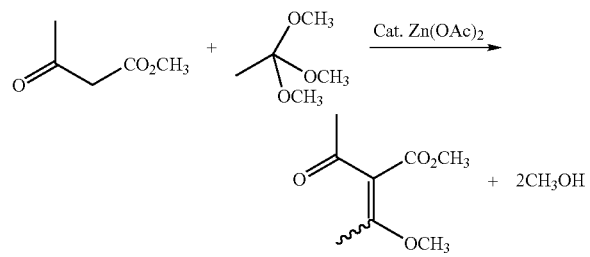

Methyl acetoacetate (108 ml, 1 mole), trimethyl orthoacetate (152 ml, 1.2 mole), zinc acetate (4.6 gm, 5 mole %) and heptane (500 ml) were charged into a 1 L 3-necked, flask (fitted with a 30 cm jacketed Vigreux fractionating column with stillhead and condenser, agitator and nitrogen inlet). The reaction was blanketed with nitrogen. The agitator was started and the flask heated to produce a very slow distillation of solvent. The distillation process was continued for 16 hours. The reaction was cooled to 20–25° C. and 350 ml methyl t-butylether was charged. The suspension was washed with 100 ml sodium citrate solution. The layers were separated and the lower aqueous layer was back extracted with 108 ml methyl t-butylether. The organic phases were combined and washed with 50 ml brine. The layers were separated and the upper organic layer was concentrated under vacuum until no more volatiles were collected at 90° C. The batch was cooled to 25–30° C., and then methyl t-butylether (324 ml), Supercel (5.0 g) and Darco (5 g) were charged to the residue. The batch was heated to reflux for 15 minutes. The batch was filtered and the Darco/Supercel cake was washed with methyl t-butylether (108 ml). The filtrate and washings were combined, then concentrated at atmospheric pressure to about 300 ml. The batch was cooled to about 25–30° C. and seeded with crystals of methyl 2-acetyl-3-methoxy-2-butenoate. The batch was continued to be cooled, and after crystallization commenced heptane (216 ml) was slowly charged over 40 minutes while continuing to cool the batch to −5° C. It was agitated at this temp for 2 hours. The batch was filtered and washed with cold 1:1 heptane/methyl t-butylether (216 ml) until the washings were colorless. The batch was dried for 6 hours under vacuum at 30° C. Yield of methyl 2-acetyl-3-methoxy-2-butenoate about 86 g. m.p 53–54° C. Physical data are reported under Example 1.

Example 3

Preparation of methyl 2-acetyl-3-methoxy-2-butenoate Using Copper Acetate Catalyst (a Comparison)

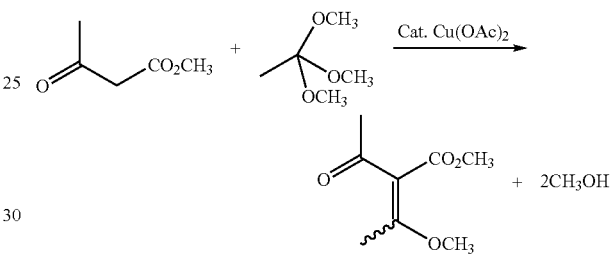

Methyl acetoacetate (108 ml, 1 mole), trimethyl orthoacetate (152 ml, 1.2 mole), copper diacetate (9 gm, 5 mole %) and toluene (540 ml) were charged into a 1 L 3-necked, flask (fitted with a 30 cm jacketed Vigreux fractionating column with stillhead and condenser, agitator and nitrogen inlet). The reaction was blanketed with nitrogen. The agitator was started and the flaks heated to produce a very slow distillation of solvent. The distillation process was continued for 15 hours. The reaction mixture was concentrated by distilling off all volatiles under low vacuum at 95° C. The residue was cooled to 20–25° C. and 324 ml methyl t-butylether were charged. The solution was extracted with 216 ml sodium citrate solution. The layers were separated and the lower aqueous layer was back extracted with 108 ml methyl t-butylether. The organic phases were combined and washed with 108 ml brine. The layers were separated, then 5 g decolorizing charcoal was charged to the upper organic layer. The suspension was refluxed for 15 minutes and then the charcoal was filtered off. The charcoal cake was washed with 216 ml methyl t-butylether. The filtrate and washings were combined, concentrated the solution of the product to 300 ml at atmospheric pressure, then cooled the solution to 20° C. and seeded the solution with crystals of the product. Cooling the batch was continued and after crystallization commenced, charging of heptane (216 ml) was slowly begun while cooling to 0° C. over 40 minutes. The batch was filtered and washed with cold 1:1 heptane/methyl t-butylether (216 ml) until the washings were colorless. The batch was dried for 6 hours under vacuum at 25° C. Yield of methyl 2-acetyl-3-methoxy-2-butenoate about 101 g. Physical data are reported under Example 1.

The following Examples illustrate the preparation of some pyrimidine-5-carboxylic acid compounds from the compound of formula 6.

Example 4

Preparation of 4,6-Dimethylpyrimidine-5-Carboxylic Acid

A. Preparation of Methyl 4,6-dimethylpyrimidine-5-carboxylate:

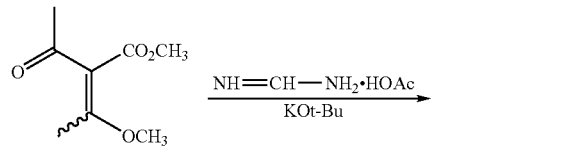

Formula 6

Methyl 2-acetyl-3-methoxy-2-butenoate (86 g), formamidine acetate (62.5 g), acetone (344 ml) and methyl alcohol (258 ml) were charged into a 2 L 3-necked, flask (fitted with addition funnel, condenser, agitator and nitrogen inlet). The reaction is blanketed with nitrogen, the agitator is started and the batch cooled to between −5 and 0° C. While the batch was cooling, a solution of potassium t-butoxide is prepared (67.4 g in THF, 258 ml) under nitrogen. When the batch reached the correct temperature, the potassium t-butoxide solution was charged slowly keeping the temperature below 5° C. The batch was allowed to warm to about 25° C. The reaction was complete after about 1.5 hours. Concentrated hydrochloric acid was added dropwise to bring the pH to 7. The batch was concentrated under vacuum until no more volatiles were collected. Methyl t-butylether (170 ml) and water (90 ml) were charged into the reaction. The batch was agitated for about 10 minutes and the layers were then separated. The lower aqueous layer was back extracted twice, each time with 170 ml methyl t-butylether. All the upper organic layers were combined and concentrated under vacuum to afford crude methyl 4,6-dimethylpyrimidine-5-carboxylate 103 gm as an oil. The product was purified by chromatography on a silica gel column eluting with heptane/ethyl acetate (7:3) followed by crystallization from heptane, m. p. 43–45° C., $^1$H NMR (CDCl$_3$): δ2.53 (6H, s, CH$_3$), δ3.96 (3H, s, OCH$_3$), δ8.96 (1H, s, ArH). $^{13}$H CMR (CDCl$_3$): δ167.97, δ164.71, δ158.23, δ53.05, δ23.18. HR-MS; Calculated for C$_7$H$_9$N$_2$O$_2$, m/z=153.0664. Found 153.0667.

B. Preparation of 4,6-Dimethylpyrimidine-5-carboxylic acid

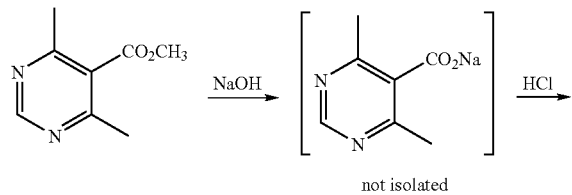

not isolated

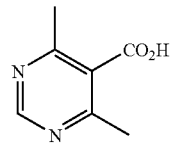

Formula 7

The crude methyl 4,6-dimethylpyrimidine-5-carboxylate from the previous example to 20° C. was cooled and water (86 ml) was charged. 25% sodium hydroxide solution (75.5 ml) was charged and the batch was warmed to 50° C. for 90 minutes. The batch was cooled to between −5 and 0° C. and concentrated hydrochloric acid was charged slowly keeping the temperature within the range of −5 to +5° C. until a pH of 1.5 was reached. The batch was agitated for at least one hour at 0° C. The batch was filtered and the product washed with ice cold water (2×43 ml). The batch was dried under vacuum at 40–45° C. Yield of 4,6-dimethylpyrimidine-5-carboxylic acid was 59 g. m. p. 203–204° C., $^1$H NMR (D$_2$O): δ2.57 (6H, s, CH$_3$), δ9.00 (1H, s, ArH). $^{13}$H CMR (D$_2$O): δ170.00, δ164.39, δ151.29, δ133.47, δ20.85. HR-MS; Calculated for C$_7$H$_9$N$_2$O$_2$, m/z=153.0664. Found 153.0667.

Example 5

Preparation of 2,4,6-Trimethylpyrimidine-5-Carboxylic Acid

A. Preparation of methyl 2,4,6-trimethylpyrimidine-5-carboxylate:

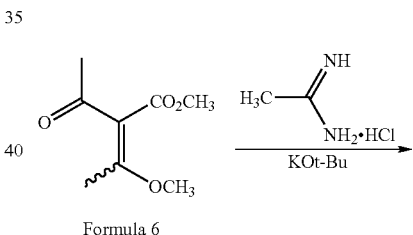

Formula 6

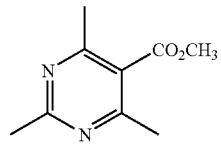

Methyl 2-acetyl-3-methoxy-2-butenoate (34.4 g, 0.2 mole), acetamidine hydrochloride (22.7 g), acetone (136 ml) and methyl alcohol (100 ml) were charged into a 1 L 3-necked, flask (fitted with addition funnel, condenser, agitator and nitrogen inlet). The reaction was blanketed with nitrogen, the agitator started and the batch cooled to between −5 and 0° C. While the batch was cooling, a solution of potassium t-butoxide was prepared (27 g in THF, 100 ml) under nitrogen. When the batch reached the correct temperature, the potassium t-butoxide solution was slowly charged, keeping the temperature below 5° C. The batch was allowed to warm to about 25° C. The reaction was complete after about 1.5 hours. Concentrated hydrochloric acid was charged dropwise to bring the pH to 7. The batch was concentrated under vacuum until no more volatiles were collected. Methyl t-butylether (140 ml) and water (85 ml) were charged. The batch was agitated for 10 minutes and the layers were then separated. The organic layer was concentrated under vacuum to afford a solid residue of methyl 2,4,6-trimethylpyrimidine-5-carboxylate, 35.8 g. The product was purified by crystallizing from methanol. m. p. 61–62° C., $^1$H NMR (CDCl$_3$): δ2.44 (6H, s, CH$_3$), δ2.61 (3H, s, CH$_3$), δ3.88 (3H, s, OCH$_3$). $^{13}$H CMR (CDCl$_3$): δ168.57, δ168.00, δ164.83, δ123.71, δ52.87, δ26.38, δ23.26. HR-MS; Calculated for C$_9$H$_{13}$N$_2$O$_2$, m/z=181.0977. Found 181.0972.

B. Preparation of 2,4,6-trimethylpyrimidine-5-carboxylic acid:

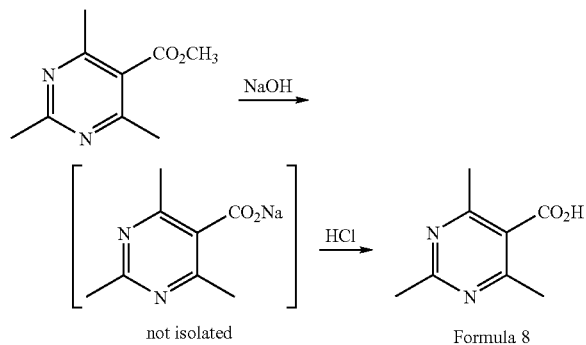

Methyl 2,4,6-trimethylpyrimidine-5-carboxylate (27 g), methanol (27 ml) and water (27 ml) were charged. 25% sodium hydroxide solution (25 ml) was charged and the batch warmed to 50° C. for 90 minutes. The batch was cooled to between −5 and 0° C. and concentrated hydrochloric acid was charged slowly, keeping the temperature within the range of −5 to +5° C. until a pH of 1.5 was reached (22.5 ml conc. HCl used). The batch was agitated for about 1.5 hours at about 2.7° C. The solid product was recovered by filtration. The batch was dried under vacuum at 40–45° C. The 2,4,6-trimethylpyrimidine-5-carboxylic acid was recrystallized from ethyl acetate. m. p. 163–164° C., $^1$H NMR (CD$_3$OD): δ2.43 (6H, s, CH$_3$), δ2.52 (3H, s, CH$_3$). $^{13}$H CMR (CD$_3$OD): δ170.42, δ168.30, δ166.09, δ126.63, δ25.64, δ22.97. HR-MS; Calculated for C$_8$H$_{11}$N$_2$O$_2$, m/z=167.0821. Found 167.0816.

Example 6

Preparation of 4,6-Dimethyl-2-Phenylpyrimidine-5-Carboxylic Acid

A. Preparation of methyl 4,6-dimethyl-2-phenylpyrimidine-5-carboxylate:

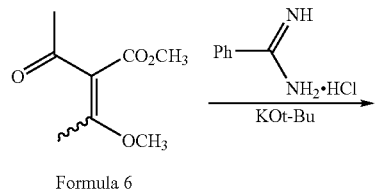

Formula 6

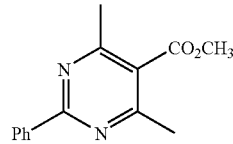

Methyl 2-acetyl-3-methoxy-2-butenoate (34.4 g, 0.2 mole), benzamidine hydrochloride (37.4 g), acetone (136 ml) and methyl alcohol (100 ml) were charged into a 1 L 3-necked, flask (fitted with addition funnel, condenser, agitator and nitrogen inlet). The reaction was blanketed with nitrogen, the agitator started and the batch cooled to between −5 and 0°C. While the batch was cooling, a solution of potassium t-butoxide was prepared (27 g in THF, 100 ml) under nitrogen. When the batch had reached the correct temperature, the potassium t-butoxide solution was charged slowly, keeping the temperature below 5° C. The batch was allowed to warm to about 25° C. The reaction was complete after about 1.5 hours. Concentrated hydrochloric acid was charged dropwise to bring the pH to 7. The batch was concentrated under vacuum until no more volatiles were collected. Methyl t-butylether (300 ml), 150 ml ethyl acetate and water (200 ml) were charged. The batch was agitated for 10 minutes, a small amount of solid was filtered off, and the layers were then separated. The organic layer was concentrated under vacuum to afford a solid residue of methyl 4,6-dimethyl-2-phenylpyrimidine-5-carboxylate, 48.7 g. m. p. 54–55° C., $^1$H NMR (CDCl$_3$): δ2.58 (6H, s, CH$_3$), δ3.89 (3H, s, OCH$_3$), δ7.42 (3H, s, ArH), δ8.40 (2H, s, ArH). $^{13}$H CMR (CDCl$_3$): δ168.78, δ165.24, δ164.11, δ137.57, δ131.34, δ128.93, δ128.92, δ124.12, δ52.86, δ23.65. HR-MS; Calculated for C$_{14}$H$_{15}$N$_2$O$_2$, m/z=243.1134. Found 243.1134.

B. Preparation of 4,6-dimethyl-2-phenylpyrimidine-5-carboxylic acid:

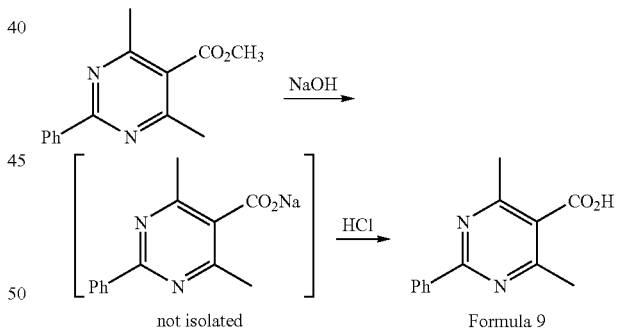

Methyl 4,6-dimethylpyrimidine-5-carboxylate (24.2 g, 0.1 mole), methanol (40 ml) and water (24 ml) were charged. 25% sodium hydroxide solution (16.6 ml) was charged and the batch warmed to 50° C. for 90 minutes. The batch was cooled to between −5 and 0° C. and concentrated hydrochloric acid was charged slowly, keeping the temperature within the range of −5 to +5° C. until a pH of 1.7 was reached (15 ml conc. HCl used). The batch was agitated for 1.5 hour at 0–5° C. The solid product was recovered by filtration and washed with cold water. The batch was dried under vacuum at 31° C. Yield of 4,6-dimethyl-2-phenylpyrimidine-5-carboxylic acid 18.3 g. m. p. 171–172° C., $^1$H NMR (CD$_3$OD): δ2.49 (6H, s, CH$_3$), δ7.35 (3H, s, ArH), δ8.29 (2H, s, ArH). $^{13}$H CMR (CD$_3$OD): δ171.06, δ166.12, δ164.99, δ138.81, δ132.42, δ129.93, δ129.88, δ126.63, δ23.50. HR-MS; Calculated for $C_{13}H_{13}N_2O_2$, m/z=229.0977. Found 229.0976.

Example 7

Preparation of E- and Z-methyl 2-acetyl-3-methoxy-2-butenoate Mixture with Pyridinium Acetate Catalyst Using Molecular Sieves to Remove Methanol

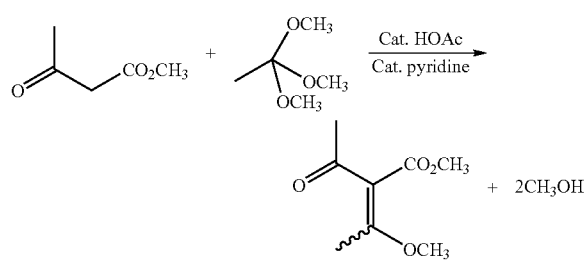

Methyl acetoacetate (108 ml, 1 mole), trimethyl orthoacetate (152 ml, 1.2 mole), toluene (270 ml), pyridine (4.1 ml, 5 mole %) and acetic acid (2.9 ml, 5 mole %) were charged to a 1 L 3-necked, flask, fitted with a Soxhlet extractor (containing 150 g 4A molecular sieves) and a reflux condenser, agitator, thermocouple and nitrogen inlet). The reaction was blanketed with nitrogen. The agitator was started and the flask heated to produce a slow reflux of the solvent. The condensate from the condenser was returned to the reaction flask through the molecular sieves in the extractor. The reaction was continued for about 12 hours. To the batch was charged additional pyridine (4.04 ml) and acetic acid (2.86 ml). The slow reflux was continued for a further 12 hours. The batch was concentrated under vacuum until no more volatiles were collected at 90° C. The batch was cooled to 25–30° C., then methyl t-butylether (324 ml), Supercel (5.0 g) and Darco (5 g) were charged to the residue. The batch was heated to reflux for 15 minutes. The batch was filtered and the Darco/Supercel cake washed with methyl t-butylether (108 ml). The filtrate and washings were combined, then concentrated at atmospheric pressure to about 300 ml. The batch was cooled to about 25–30° C. and seeded with crystals of methyl 2-acetyl-3-methoxy-2-butenoate. The cooling of the batch was continued and after crystallization commenced, heptane (216 ml) was slowly charged over 40 minutes while continuing to cool the batch to −5° C. It was agitated at this temp for 2 hours. The batch was filtered and washed with cold 1:1 heptane/methyl t-butylether (216 ml) until the washings were colorless. The batch was dried for 6 hours under vacuum at 30° C. Yield of methyl 2-acetyl-3-methoxy-2-butenoate: about 100 g. Physical data are reported under Example 1.

Example 8

Preparation of E- and Z-methyl 2-acetyl-3-methoxy-2-butenoate Mixture with Pyridinium Propionate Catalyst

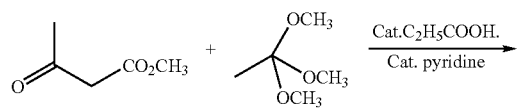

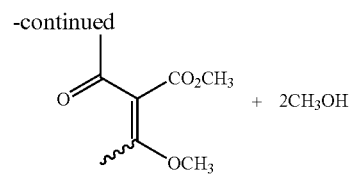

Methyl acetoacetate (108 ml, 1 mole), trimethyl orthoacetate (152 ml, 1.2 mole), toluene (270 ml), pyridine (4.1 ml, 5 mole %) and propionic acid (3.7 ml, 5 mole %) were charged to a 1 L 3-necked, flask (fitted with a 30 cm vacuum jacketed Vigreux fractionating column with stillhead and condenser, agitator, thermocouple and nitrogen inlet). The reaction was blanketed with nitrogen. The agitator was started and the flask heated to produce a very slow distillation of solvent. The heating was adjusted so that the solvent distilled at about the boiling point of the methanol/toluene azeotrope (64° C.). The distillation process was continued for about 12 hours. Additional pyridine (4.1 ml) and propionic acid (3.7 ml) were charged to the flask. The slow distillation was continued for a further 12 hours. The batch was concentrated under vacuum until no more volatiles were collected at 90° C. The batch was cooled to 25–30° C., then methyl t-butylether (324 ml), Supercel (5.0 g) and Darco (5 g) were charged to the residue. The batch was heated to reflux for 15 minutes. The batch was filtered and the Darco/Supercel cake was washed with methyl t-butylether (108 ml). The filtrate and washings were combined and concentrated at atmospheric pressure to about 300 ml. The batch was cooled to about 25-30° C. and seeded with crystals of methyl 2-acetyl-3-methoxy-2-butenoate. The cooling of the batch was continued and after crystallization commenced, heptane (216 ml) was slowly charged over 40 minutes while continuing to cool the batch to −5° C. It was agitated at this temp for 2 hours. The batch was filtered and washed with cold 1:1 heptane/methyl t-butylether (216 ml) until the washings were colorless. The batch was dried for 6 hours under vacuum at 30° C. Yield of methyl 2-acetyl-3-methoxy-2-butenoate: about 100 g. Physical data are reported under Example 1.

Example 9

Preparation of E- and Z-ethyl 2-acetyl-3-ethoxy-2-butenoate Mixture with Pyridinium Acetate Catalyst

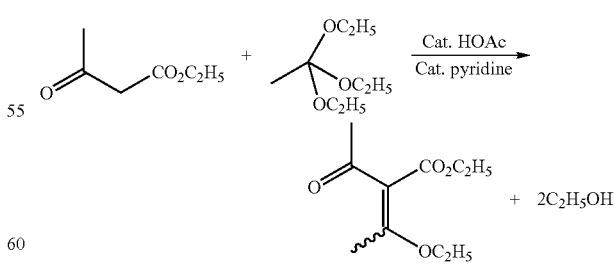

Ethyl acetoacetate (127 ml, 1.0 mole), triethyl orthoacetate (216 ml, 1.4 mole), toluene (400 ml), pyridine (8.2 ml, 10 mole %) and acetic acid (5.8 ml, 10 mole %) were charged to a 1 L, 3-necked, flask (fitted with a 30 cm vacuum jacketed Vigreux fractionating column with stillhead and condenser, agitator, thermocouple and nitrogen inlet). The reaction was blanketed with nitrogen. The agitator was started and the flask heated to produce a very slow distillation of solvent. The heating was adjusted so that the solvent distilled at about the boiling point of the ethanol/toluene azeotrope (77° C.). The distillation was continued for about 17 hours. The batch was concentrated under low vacuum until no more volatiles were collected at 90° C. The residual oil was distilled at 0.5 mm Hg collecting the fraction b. pt 85–86° C. Yield of ethyl 2-acetyl-3-ethoxy-2-butenoate about 117 g. $^1$H NMR (CDCl$_3$): δ1.27,1.33 (6H, 2t, CH$_3$), δ2.19, 2.35, 2.35, 2.44 (12H, 4s, CH$_3$), δ4.08 (4H, 2q, CH$_2$), δ 4.19 (2H, q, CH$_2$), δ4.29, (2H, q, CH$_2$). $^{13}$H CMR (CDCl$_3$): δ200.37, δ194.76, δ171.40, δ168.91, δ168.47, δ166.64, δ116.49, δ116.44, δ64.47, δ64.26, δ61.37, δ60.78, δ32.09, δ30.23, δ15.47, δ15.42, δ15.37, δ15.22, δ14.53, δ14.50. HR-MS: Calculated for C$_{10}$H$_{17}$O$_4$, m/z=201.1127. Found 201.1127.

Example 10

Preparation of E- and Z-methyl 2-propionyl-3-methoxy-2-butenoate Mixture Using Pyridinium Acetate Catalyst

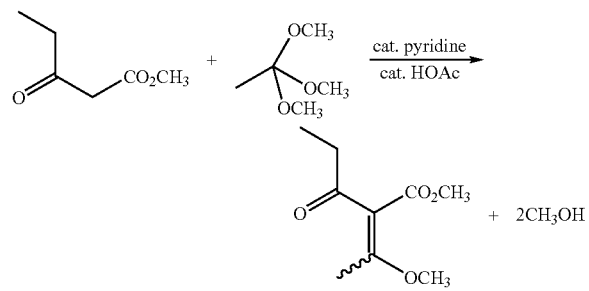

Methyl 3-oxopentanoate (126 ml, 1.0 mole), trimethyl orthoacetate (178 ml, 1.4 mole), toluene (400 ml), pyridine (4.1 ml, 5 mole %) and acetic acid (2.9 ml, 5 mole %) were charged to a 1 L 3-necked, flask (fitted with a 30 cm vacuum jacketed Vigreux fractionating column with stillhead and condenser, agitator, thermocouple and nitrogen inlet). The reaction was blanketed with nitrogen. The agitator was started and the flask heated to produce a very slow distillation of solvent. The heating was adjusted so that the solvent distilled at about the boiling point of the methanol/toluene azeotrope (64° C.). The distillation process was continued for about 8 hours. Additional toluene (150 ml), pyridine (4.1 ml, 5 mole %) and acetic acid (2.9 ml, 5 mole %) were charged to the reaction and the slow distillation of the methanol/toluene azeotrope continued for a further 8 hours. The batch was concentrated under low vacuum until no more volatiles were collected at 90° C. The batch was cooled to 25–30° C. The residual oil was distilled at 0.5 mm Hg collecting the fraction b. pt 72–73° C. Yield of E and Z methyl 2-propionyl-3-methoxy-2-butenoate: 78 g. $^1$H NMR (CDCl$_3$): δ0.89, 0.90 (2t, CH$_3$), δ2.23, 2.24 (2s, CH$_3$), δ2.27, 2.44 (2m, CH$_2$), δ3.52 (s, OCH$_3$), δ3.55 (s, OCH$_3$), δ3.59 (s, OCH$_3$), δ3.64 (s, OCH$_3$). $^{13}$H CMR (CDCl$_3$): δ204.42, δ198.03, δ171.16, δ169.25, δ169.07, δ166.59, δ115.65, δ114.93, δ55.70, δ55.65, δ51.98, δ51.84, δ37.53, δ35.31, δ14.88, δ14.52, δ8.53, δ8.28. HR-MS: Calculated for C$_9$H$_{15}$O$_4$, m/z=187.0970. Found 187.0969.

Example 11

Preparation of 4-Ethyl-6-methylpyrimidine-5-Carboxylic Acid

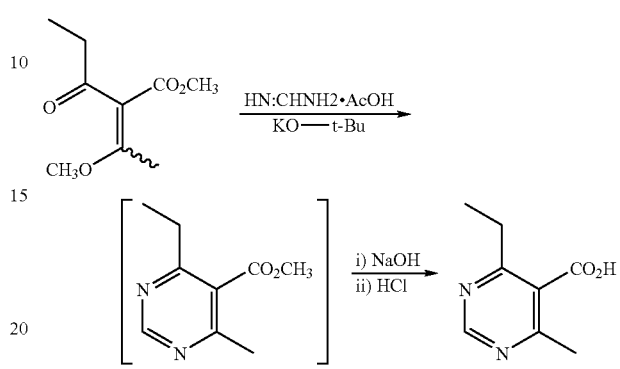

A. Preparation of Methyl 4-Ethyl-6-methylpyrimidine-5-carboxylate

A mixture of E- and Z-methyl 2-propionyl-3-methoxy-2-butenoate (as prepared in example 10) was reacted with formamidine acetate and potassium butoxide in a manner similar to that in example 4A to afford crude methyl 4-ethyl-6-methylpyrimidine-5-carboxylate as an oil. NMR (CDCl$_3$): δ1.27 (3H, t, CH$_3$), δ2.51 (3H, s, CH$_3$), δ2.76 (2H, q, CH$_2$), δ3.95 (3H, s, OCH$_3$), δ7.28 (1H, s, ArH). $^{13}$H CMR (CDCl$_3$): δ168.66, δ168.13, δ164.37, δ158.50, δ126.57, δ53.01, δ29.60, δ22.99, δ13.23. HR-MS; Calculated for C$_9$H$_{13}$N$_2$O$_2$, m/z=181.0977. Found 181.0973.

B. Preparation of 4-Ethyl-6-methylpyrimidine-5-carboxylic acid

The crude methyl 4-ethyl-6-methylpyrimidine-5-carboxylate from example 11A was reacted with 25% sodium hydroxide solution and then with concentrated hydrochloric acid in a manner similar to example 4B to give 4-ethyl-6-methylpyrimidine-5-carboxylic acid, m. p. 133–134° C., $^1$H NMR (CDCl$_3$): δ1.24 (3H, t, CH$_3$), δ2.56 (3H, s, CH$_3$), δ2.85 (2H, q, CH$_2$) δ9.02 (1H, s, ArH), δ11.93 (1H, s, OH). $^{13}$H CMR (CDCl$_3$): δ169.58, δ169.52, δ164.80, δ157.32, δ127.65, δ29.51, δ22.74, δ13.68. HR-MS; Calculated for C$_8$H$_9$N$_2$O$_2$, m/z=165.0664. Found 165.0666.

Example 12

Preparation of 2,4-Dimethyl-6-ethylpyrimidine-5-Carboxylic Acid

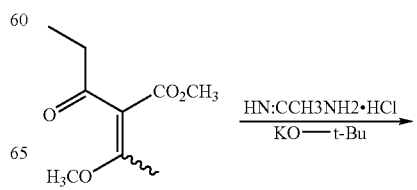

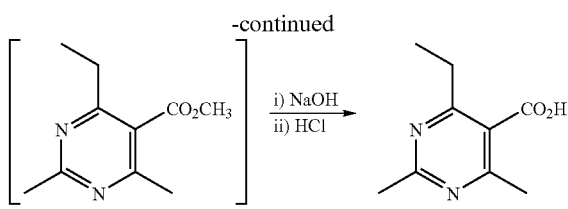

A. Preparation of methyl 2,4-dimethyl-6-ethylpyrimidine-5-carbox-ylate:

A mixture of E- and Z-methyl 2-propionyl-3-methoxy-2-butenoate (as prepared in example 10) was reacted with acetamidine hydrochloride and potassium butoxide in a manner similar to that in example 5A to afford crude methyl 2,4-dimethyl-6-ethylpyrimidine-5-carboxylate as an oil. NMR (CDCl$_3$): δ1.21 (3H, t, CH$_3$), δ2.44 (3H, s, CH$_3$), δ2.63 (3H, s, CH$_3$), δ2.67 (2H, q, CH$_2$), δ3.87 (3H, s, OCH$_3$). $^{13}$H CMR (CDCl$_3$): δ169.17, δ168.82, δ168.18, δ164.54, δ123.39, δ52.90, δ29.78, δ26.45, δ23.11, δ13.71. HR-MS; Calculated for C$_{10}$H$_{14}$N$_2$O$_2$, m/z=194.1055. Found 194.1048.

B. Preparation of 2,4-dimethyl-6-ethylpyrimidine-5-carboxylic acid:

The crude methyl 2,4-dimethyl-6-ethylpyrimidine-5-carboxylate from example 12A was reacted with 25% sodium hydroxide solution and then with concentrated hydrochloric acid in a manner similar to example 5B to give 4,6-dimethyl-6-ethylpyrimidine-5-carboxylic acid, m. p. 167–168° C., $^1$H NMR (DMSO): δ0.37 (3H, t, CH$_3$), δ1.69 (3H, s, CH$_3$), δ1.79 (3H, s, CH$_3$), δ1.98 (2H, q, CH$_2$), δ2.37 (1H, s, OH). $^{13}$H CMR (DMSO): δ167.84, δ167.81, δ165.81, δ163.09, δ123.60, δ27.68, δ22.92, δ20.06, δ11.43. HR-MS; Calculated for C$_9$H$_{12}$N$_2$O$_2$, m/z=180.0899. Found 180.0903.

Example 13

Preparation of
4ethyl-6-methyl-2-phenylpyrimidine-5-Carboxylic Acid

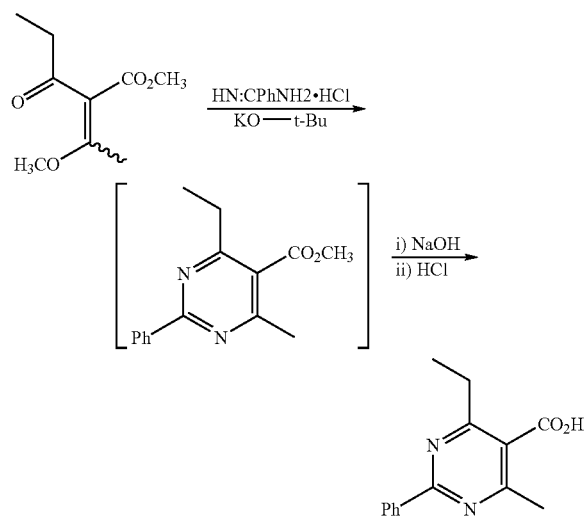

A. Preparation of methyl 4-ethyl-6-methyl-2-phenylpyrimidine-5-carboxylate

A mixture of E- and Z-methyl 2-propionyl-3-methoxy-2-butenoate (as prepared in example 10) was reacted with benzamidine hydrochloride and potassium butoxide in a manner similar to that in example 6A to afford crude methyl 4-ethyl-6-methyl-2-phenylpyrimidine-5-carboxylate as an oil. NMR (CDCl$_3$): δ1.28 (3H, t, CH$_3$), δ2.51 (3H, s, CH$_3$), δ2.76 (2H, q, CH$_2$), δ3.88 (3H, s, OCH$_3$), δ7.40 (3H, m, ArH), δ8.41 (2H, d, ArH). $^{13}$H CMR (CDCl$_3$): δ169.27, δ168.98, δ164.87, δ164.15, δ123.39, δ137.76, δ131.27, δ129.27, δ128.93, δ128.88, δ123.89, δ52.89, δ29.68, δ23.51, δ13.18. HR-MS; Calculated for C$_{15}$H$_{17}$N$_2$O$_2$, m/z=257.1290. Found 2571295.

B. Preparation of 4-ethyl-6-methyl-2-phenylpyrimidine-5-carboxylic acid:

The crude methyl 4-ethyl-6-methyl-2-phenylpyrimidine-5-carboxylate from example 13A was reacted with 25% sodium hydroxide solution and then with concentrated hydrochloric acid in a manner similar to example 6B to give 4-ethyl-6-methyl-2-phenylpyrimidine-5-carboxylic acid, m. p. 136–137° C., $^1$H NMR (CDCl$_3$): δ1.33 (3H, t, CH$_3$), δ2.66 (3H, s, CH$_3$), δ2.94 (2H, q, CH$_2$), δ7.44 (3H, m, ArH), δ8.40 (2H, 2, ArH), δ10.32 (1H, s, OH). $^{13}$H CMR (CDCl$_3$): δ171.67, δ169.15, δ164.52, δ163.14, δ135.98, δ130.39, δ127.95, δ121.72, δ28.45, δ22.51, δ11.67. HR-MS; Calculated for C$_{14}$H$_{15}$N$_2$O$_2$, m/z=243.1134. Found 243.1129.

As stated earlier, the pyrimidine carboxylic acids, shown above, can be utilized as intermediates for the synthesis of a variety of pharmaceutical, herbicidal and insecticidal agents. In particular, these intermediates are useful precursors to a variety of CCR5 inhibitors. They are particularly useful for the preparation of, for example, the compound of Formula C.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A process for preparing a compound represented by the structural Formula 3:

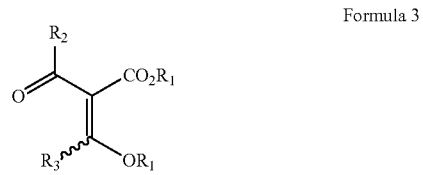

Formula 3 wherein R$^1$ is lower alkyl; and R$^2$ and R$^3$ can be the same or different, each being independently selected from the group consisting of alkyl, aryl and aralkyl; said process comprising:

reacting a 3-keto ester compound of Formula 1:

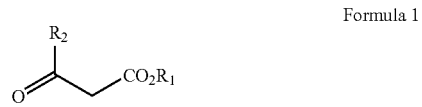

Formula 1 with an ortho ester compound of Formula 2:

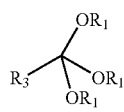
Formula 2 in the presence of at least one solvent and at least one tert-amine carboxylate salt as catalyst, to yield said compound of Formula 3.

2. The process according to claim 1, wherein $R^2$ and $R^3$ are the same or different, each being an alkyl.

3. The process according to claim 2, wherein said alkyl is a lower alkyl.

4. The process of claim 3, wherein $R^1=R^2=R^3=$methyl.

5. The process according to claim 1, wherein said tert-amine carboxylate salt is an acetate, propionate, stearate or benzoate salt of pyridine, lutidine, quinoline, triethylamine, diethylisopropylamine, tributylamine, N-methylmorpholine or N-methylpiperidine.

6. The process according to claim 5, wherein said tert-amine catalyst is pyridinium acetate, triethylamine acetate, lutidine acetate, pyridinium propionate, triethylamine propionate or lutidine propionate.

7. The process according to claim 6, wherein said catalyst is pyridinium acetate or pyridinium propionate.

8. The process according to claim 7, wherein said pyridinium acetate or pyridinium propionate is formed in situ.

9. The process according to claim 7, wherein said catalyst is pyridinium acetate.

10. The process according to claim 1, wherein the catalyst is soluble in the solvent system.

11. The process according to claim 1, wherein the reaction is performed at about the reflux temperature of said solvent.

12. The process according to claim 1, wherein said catalyst is used in amounts from about 1 mole % to about 50 mole % with respect to said 3-keto ester.

13. The process according to claim 12, wherein said catalyst is used in amounts from about 5 mole % to about 10 mole % with respect to said 3-keto ester.

14. The process according to claim 1, wherein said solvent is selected from the group consisting of: aliphatic hydrocarbons, alicyclic hydrocarbons, aromatic hydrocarbons, esters, ethers, chlorinated hydrocarbons and mixtures thereof.

15. The process according to claim 14, wherein said solvent is selected from the group consisting of aliphatic hydrocarbons, alicyclic hydrocarbons and aromatic hydrocarbons.

16. The process according to claim 15, wherein said solvent is selected from toluene, benzene, heptane, cyclohexane, methylcyclohexane and mixtures thereof.

17. The process according to claim 16, wherein said solvent is toluene.

18. The process according to claim 16, wherein said solvent is heptane.

19. The process according to claim 1, wherein said tertiary amine carboxylic acid salt catalyst is present in from about 1 mole % to about 50 mole % with respect to said 3-keto ester; said solvent is toluene; and said reaction is performed at about the reflux temperature of the solvent.

20. A process for preparing the compound of the structural Formula 6, comprising reacting a compound of Formula 4:

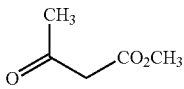
Formula 4 with a compound of Formula 5:

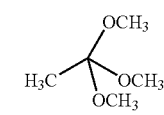
Formula 5 in the presence of at least one solvent and at least one tert-amine carboxylate salt as catalyst, to yield the compound of Formula 6:

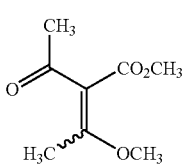
Formula 6

21. The process according to claim 20, wherein said tert-amine carboxylate salt is an acetate, propionate, stearate or benzoate salt of pyridine, lutidine, quinoline, triethylamine, diethylisopropylamine, tributylamine, N-methylmorpholine or N-methylpiperidine.

22. The process according to claim 21, wherein said tert-amine catalyst is pyridinium acetate, triethylamine acetate, lutidine acetate, pyridinium propionate, triethylamine propionate or lutidine propionate.

23. The process according to claim 22, wherein said catalyst is pyridinium acetate or pyridinium propionate.

24. The process according to claim 20, wherein the reaction is performed at about the reflux temperature of said solvent.

25. The process according to claim 20, wherein said catalyst is used in amounts from about 1 mole % to about 50 mole % with respect to said compound of Formula 4.

26. The process according to claim 25, wherein said catalyst is used in amounts from about 5 mole % to about 10 mole % with respect to said compound of Formula 4.

27. The process according to claim 20, wherein said solvent is selected from the group consisting of: aliphatic hydrocarbons, alicyclic hydrocarbons, aromatic hydrocarbons, ethers, chlorinated hydrocarbons and mixtures thereof.

28. The process according to claim 27, wherein said solvent is selected from the group consisting of aliphatic hydrocarbons, alicyclic hydrocarbons and aromatic hydrocarbons.

29. The process according to claim 28, wherein said solvent is selected from toluene, benzene, heptane, cyclohexane, methylcyclohexane and mixtures thereof.

30. The process according to claim 29, wherein said solvent is toluene.

31. The process according to claim 29, wherein said solvent is heptane.

32. The process according to claim 20, wherein said reaction is performed at about the reflux temperature of said solvent.

33. The process according to claim 20, wherein the compound of Formula 6 is isolated by crystallization.

34. The process according to claim 33, wherein said crystallization is from methyl t-butylether alone or in combination with a non-polar anti-solvent.

35. The process according to claim 34, wherein said anti-solvent is heptane.

* * * * *